United States Patent
Wang et al.

(10) Patent No.: US 7,845,581 B2
(45) Date of Patent: Dec. 7, 2010

(54) AIR FRESHENER

(75) Inventors: Yuhua Wang, Beijing (CN); Lun Chai, Hong Kong (CN)

(73) Assignee: Winplus Company Limited, Shatin, N.T. (HK)

( * ) Notice: Subject to any disclaimer, the term of this patent is extended or adjusted under 35 U.S.C. 154(b) by 147 days.

(21) Appl. No.: 12/294,197

(22) PCT Filed: Sep. 28, 2006

(86) PCT No.: PCT/CN2006/002552

§ 371 (c)(1),
(2), (4) Date: Sep. 23, 2008

(87) PCT Pub. No.: WO2007/109934

PCT Pub. Date: Oct. 4, 2007

(65) Prior Publication Data

US 2009/0230210 A1     Sep. 17, 2009

(30) Foreign Application Priority Data

Mar. 28, 2006   (CN)  .................. 2006 2 0018607 U

(51) Int. Cl.
*A24F 25/00* (2006.01)
(52) U.S. Cl. .......................................... 239/58; 239/59
(58) Field of Classification Search ............. 239/34, 239/43, 44, 47, 51.5, 53–60
See application file for complete search history.

(56) References Cited

U.S. PATENT DOCUMENTS

| 4,340,168 A | * | 7/1982 | Webinger | ............... 229/125.19 |
| 5,004,138 A | | 4/1991 | Gabas | |
| 5,148,984 A | | 9/1992 | Bryson, Jr. | |
| 5,527,493 A | * | 6/1996 | McElfresh et al. | ............ 261/30 |
| 5,782,409 A | * | 7/1998 | Paul | .............................. 239/56 |
| 6,367,184 B1 | * | 4/2002 | Kheder | ......................... 40/617 |
| 2003/0075613 A1 | | 4/2003 | Brown | |
| 2005/0001053 A1 | | 1/2005 | Zobele | |

FOREIGN PATENT DOCUMENTS

| CN | 2165497 Y | 5/1994 |
| CN | 1090124 A1 | 8/1994 |
| CN | 2277963 Y | 4/1998 |
| CN | 2323788 Y | 6/1999 |
| CN | 2348851 Y | 11/1999 |
| CN | 1485253 A | 3/2004 |
| CN | 1579888 A | 2/2005 |
| CN | 2712358 Y | 7/2005 |
| CN | 2749503 Y | 1/2006 |
| CN | 2753370 Y | 1/2006 |
| JP | 10-258116 A | 9/1998 |
| JP | 200379712 A | 3/2003 |

* cited by examiner

*Primary Examiner*—Davis Hwu
(74) *Attorney, Agent, or Firm*—The Webb Law Firm

(57) ABSTRACT

An air freshener of the invention includes a slideable box molded from thermoplastics, a holding jacket, a fixing device, and an essence box made of plastics and filled with liquid essence. The air freshener of the invention can be used inside a car or a room, and is capable of adjusting the release rate of the diffused essence gas.

5 Claims, 4 Drawing Sheets

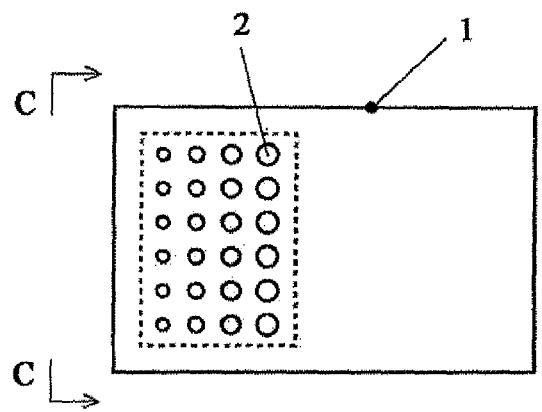
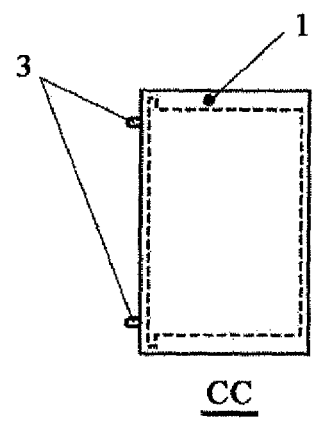
FIG. 1a  FIG. 1b
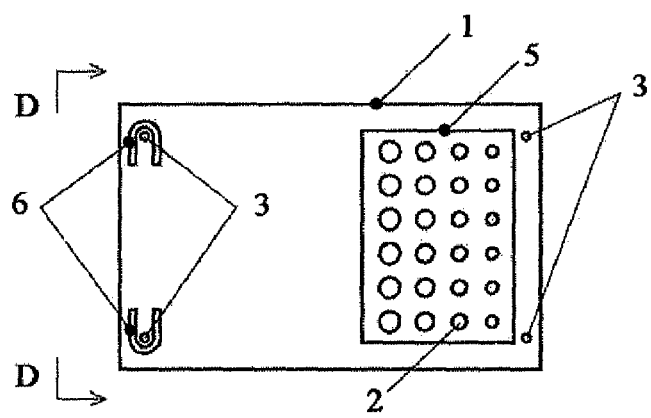
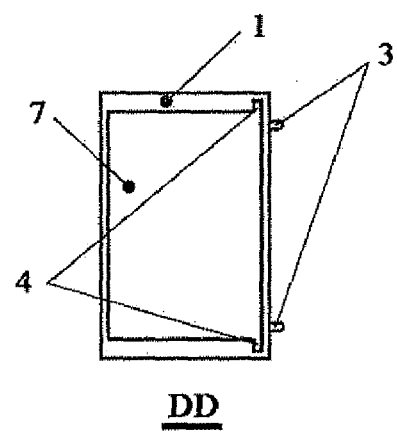
FIG. 1c  FIG. 1d
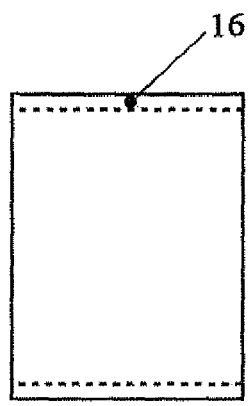
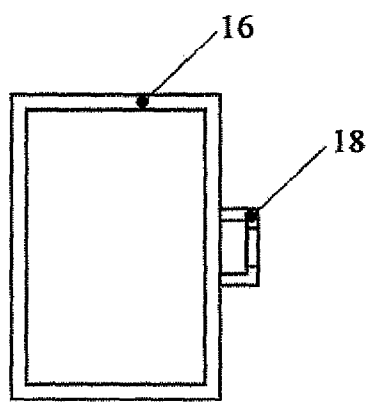
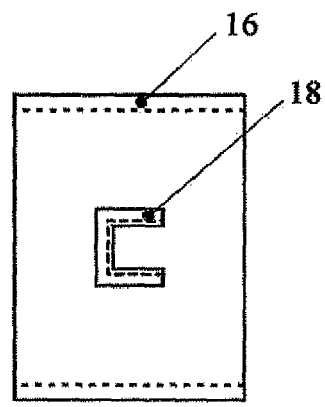
FIG. 2a  FIG. 2b  FIG. 2c

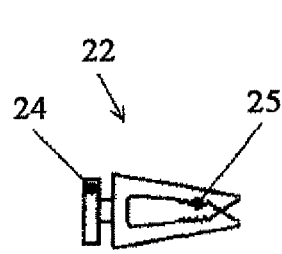
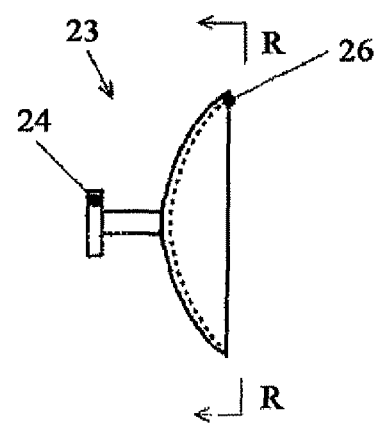
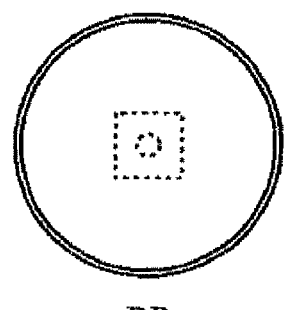
FIG. 3a  FIG. 3b  FIG. 3c
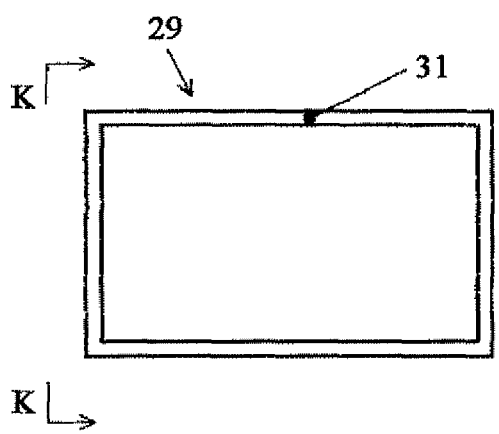
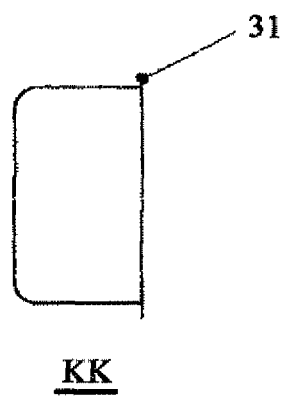
FIG. 4a  FIG. 4b
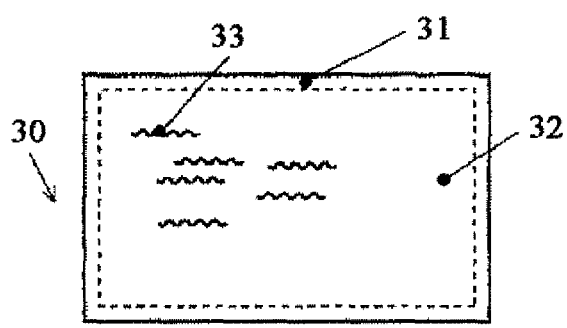
FIG. 5

AIR FRESHENER

FIELD OF THE INVENTION

The present invention relates to an air freshener.

BACKGROUND OF THE INVENTION

The prior art air fresheners have various disadvantages.

SUMMARY OF THE INVENTION

The object of the present invention is to provide an air freshener which can overcome the disadvantages existing in the prior art air fresheners.

The air freshener according to the invention comprises: a slideable box molded from thermoplastics; a holding jacket; a fixing device (a fixing clip or a suction cup); and an essence (or called as "perfume") box made of plastics and filled with liquid essence, wherein the slideable box is in a shape of a hexahedron having approximately a rectangular or square cross-section, and one side (wall) of the slideable box is opened and is sized to just allow the essence box to pass-through. A window which allows essence gas (or called as "perfume vapor") to be released is formed on the back side of the slideable box. The essence box comprises a box body which is suction molded from transparent plastic sheet materials, a semi-permeable film which is impermeable to the liquid essence and is permeable to the essence gas, and an aluminum foil-plastic composite film which prevents the essence gas from being diffused from the essence box (30, 35, 38) before use According to the air freshener of the invention, the holding jacket is in a shape of a hexahedron having approximately a rectangular or square cross-section. A pair of opposite sides of the hexahedron are opened and thus the hexahedron forms a jacket. The holding jacket just surrounds (envelopes or encloses) the slideable box. A clipping groove for clipping the fixing device is provided on the back side of the holding jacket.

According to the air freshener of the invention, the essence box is shaped and sized to be just embeddable in the slideable box. When the holding jacket surrounds the slideable box, the slideable box can slide back and forth in the holding jacket in order to change the size of the window which allows the essence gas to be released, so that the release area of the essence gas is increased or reduced, and the release rate of the essence gas can be adjusted accordingly.

According to the air freshener of the invention, the fixing device is a fixing clip which can be clipped on a grille of an air outlet of an air conditioner in a vehicle.

According to the air freshener of the invention, the fixing device is a suction cup which has a vacuum suction cup.

According to the air freshener of the invention, the suction cup is made from soft plastics (typically polyvinyl chloride); the box body of the essence box is made of a transparent sheet material (typically polyester); and the slideable box, the holding jacket and the fixing clip are made from polypropylene.

The air freshener of the invention can be used inside a car or a room to freshen the air therein, and can adjust the release rate of the diffused essence gas.

BRIEF DESCRIPTION OF THE DRAWINGS

FIG. 1 (FIGS. 1a, 1b, 1c and 1d) are schematic views of the slideable box of the air freshener of the present invention.

FIG. 2 (FIGS. 2a, 2b and 2c) are schematic views of the holding jacket of the air freshener of the invention.

FIG. 3 (FIGS. 3a, 3b and 3c) are schematic views of the fixing device (a fixing clip and a suction cup) of the air freshener of the invention.

FIG. 4 (FIGS. 4a and 4b) are schematic views of the essence box of the air freshener of the invention.

FIG. 5 is a schematic view of the essence box of the air freshener of the invention, wherein the essence box is filled with liquid essence and sealed with a semi-permeable plastic film.

DETAILED DESCRIPTION OF THE PREFERRED EMBODIMENTS

Figure 6A:
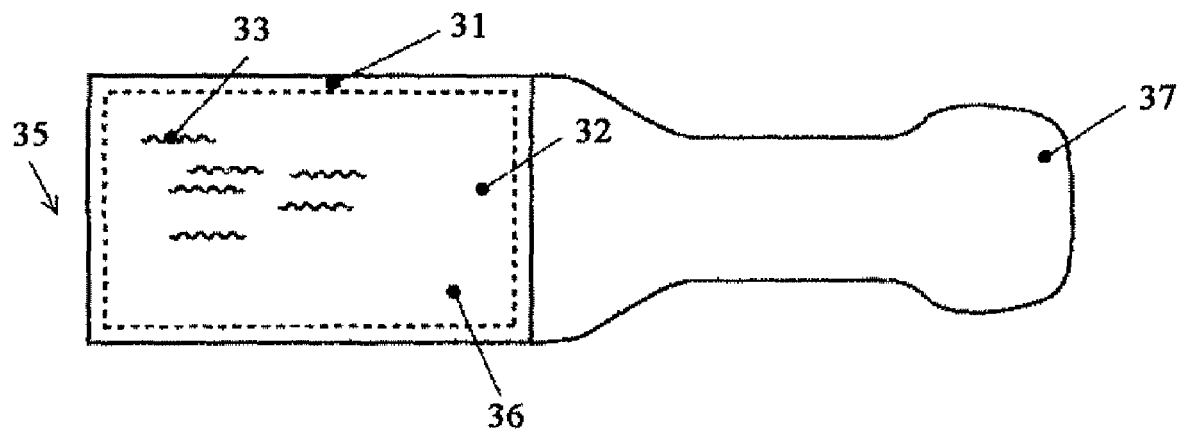
FIG. 6 (FIGS. 6a and 6b) are schematic views of the essence box of the air freshener of the invention, wherein an aluminum foil-plastic composite film is additionally attached (laminated) to the semi-permeable seal film and the aluminum foil-plastic composite film is partially torn off.

FIGS. 1a, 1b, 1c and 1d are schematic views of the slideable box 1 of the air freshener of the present invention, wherein FIG. 1a is a front view, FIG. 1b is a side view along Line C-C of FIG. 1a, and FIG. 1c is a back view.

The slideable box 1 is in a shape of a hexahedron having approximately a rectangular or square cross-section. The slideable box 1 may be in a shape other than the above shape. As seen from FIG. 1b, the slideable box is sealed at its left end. As seen from FIG. 1d, the slideable box is opened at its right end and thus has a space 7 for inserting an essence box. The edge 31 of the essence box is inserted into a groove 4 formed on the slideable box, so that the essence box and the slideable box can be engaged together A number of viewports 2 of different or equal sizes are formed on the front side of the slideable box 1 (FIG. 1a), so that a consumer can see the liquid essence in the essence box. A window 5 allowing the essence gas to be released and a plurality of projections 3 (refer to FIG. 1c) defining the sliding range of the slideable box 1 within the holding jacket 16 described later are formed on the back side of the slideable box 1 (FIG. 1c). U-shaped slots 6 are formed around two projections 3 which are positioned close to the left end of the slideable box (FIG. 1c). When inserting the slideable box 1 into the holding jacket 16, the two projections 3 are pressed down so that the slideable box 1 can be inserted. When the slideable box is inserted into the holding jacket 16 completely, the two projections 3 return to their original position by means of elasticity, and the slideable box is confined to slide back and forth between the projections 3 positioned close to both ends of the slideable box and can't drop off.

FIGS. 2a, 2b and 2c are schematic views of the holding jacket 16 of the air freshener of the invention, wherein FIG. 2a is a front view, FIG. 2b is a side view, and FIG. 2c is a back view. The holding jacket 16 is in a shape of a hollowed hexahedron having approximately a rectangular or square cross-section. The holding jacket 16 may be in a shape other than the above shape. A pair of opposite sides of the hexahedron are opened so that the hexahedron becomes a jacket. The holding jacket 16 may just surround the slideable box 1 so that they are closely fitted together. A clipping groove 18 for clipping a fixing device described later is provided on the back side of the holding jacket 16.

FIGS. 3a, 3b and 3c are schematic views of the fixing device (a fixing clip 22 and a suction cup 23) of the air freshener of the invention, wherein FIG. 3a shows the fixing clip 22, FIG. 3b shows the suction cup 23, and FIG. 3c is a back view of the suction cup 23 along Line R-R of FIG. 3b.

In FIG. 3a, a clip head 24 of the fixing clip 22 can engage into the clipping groove 18 of the holding jacket 16, and a pair of the clip arms 25 of the fixing clip 22 may be clipped on a grille of an air outlet of an air conditioner of a vehicle so that the air freshener of the invention is fixed in place and emits essence gas. The emitted essence gas can be diffused with the help of wind blown from the air outlet of the air conditioner.

In FIG. 3b, the suction cup 23 is made of a soft plastic material (typically polyvinyl chloride). One end of the suction cup 23 is formed as a clip head 24, and the other end of the suction cup 23 is formed as a "vacuum suction cup" 26. The clip head 24 can be engaged into the clipping groove 18 of the holding jacket 16, and the "vacuum suction cup" 26 enables the air freshener of the present invention to be fixed on a smooth surface such as a surface of window glass inside a vehicle, or any smooth surfaces inside a room or a vehicle.

The above-mentioned components are typically molded from thermoplastics by injection molding. The suction cup 23 is typically made of a soft plastic material (such as polyvinyl chloride); other components are typically made of hard plastic materials such as ABS, polystyrene, polypropylene, nylon and polyester etc.

FIGS. 4a to 6b are views showing the structure of essence boxes 30, 35 and 38.

As seen from FIGS. 4a and 4b, the box body 29 of the essence box 30 (35, 38) is typically formed by "bubble cap" type suction molding from a transparent plastic sheet material such as polyester or polyvinyl chloride. Preferably, the polyester sheet material is used because this material doesn't react with the chemical substance of the essence The transparent material is used so that a consumer can view the liquid essence inside the essence box. The box body 29 is in a shape of a hexahedron having approximately a rectangular or square cross-section. The box body 29 may be in a shape other than the above shape. The box body 29 has an opened side. An edge 31 in the same plane is formed along the periphery of the opened side.

FIG. 5 is a schematic view of the essence box 30 of the invention (essence box 35 in FIG. 6a and essence box 38 in FIG. 6b) filled with a liquid essence therein and sealed with a plastic film. In FIG. 5, the box body 29 of the essence box 30 (35, 38) is sealed by a layer of extremely-thin semi-permeable film 32 attached along the plane of the edge 31 so as to form a closed space in which liquid essence 33 is filled inside the box body 29. The semi-permeable film 32 has a characteristic of preventing the liquid essence 33 from leaking from the box body 29 but allowing the volatilized perfume vapor molecules to emit from the box body 29 so that scent of the essence gas can be smelt outside the box body 29. The semi-permeable film 32 may be a film with thickness of about several micrometers, but other films which are thinner or thicker may also be used as the semi-permeable film 32.

Figure 6B:
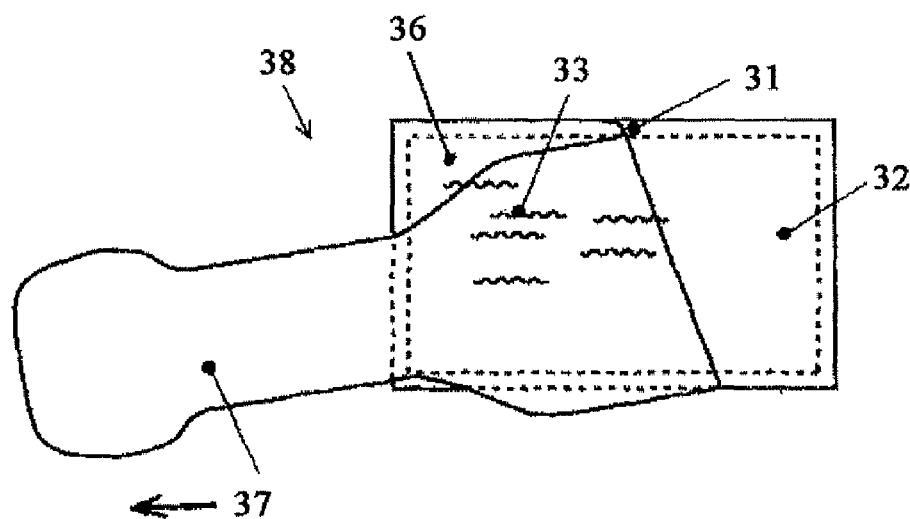

FIG. 6 shows the essence box 30 (35, 38) of the air freshener in the ready-to-use state. Since it usually takes a quite long time for the essence box 30 (35, 38) from the factory to the consumer, a layer of airtight aluminum foil-plastic composite film 36 and 37 (as shown in FIG. 6a) is additionally attached to the semi-permeable film 32 in order to prevent the essence from volatilizing and escaping from the essence box before use. The aluminum foil-plastic composite film 36 and 37 is also attached to the semi-permeable film 32 along the edge 31 of the box body 29. The condition of performing sealing and attaching is controlled so that the semi-permeable film 32 is attached to the edge 31 of the box body 29 firmly so as not to be torn off, while the aluminum foil-plastic composite film 36 and 37 is attached to the semi-permeable film 32 moderately so as to be easily torn off from the semi-permeable film 32 without damaging the sealing between the semi-permeable film 32 and the edge 31 of the box body 29. FIG. 6b shows the state in which the aluminum foil-plastic composite film 36 and 37 is partially torn off.

The essence used in the essence box 30 (35, 38) of the air freshener of the present invention may be a perfume formulated with various aroma materials in accordance with a formula in a factory or a perfume obtained by dilution with solvent (typically ethanol or isopropyl alcohol, or other organic solvents) according to a certain proportion. A dye can also be added into the essence or perfume in the essence box 30 (35, 38) so that the essence or perfume have different colors which can be used to substantially indicate the types of the fragrance (for example, the fragrance of strawberry is indicated by red, the fragrance of rose is indicated by pink, the fragrance of lavender is indicated by purple and the fragrance of lemon is indicated by yellow etc). In addition, a trademark or aesthetic patterns may be formed or printed on external surfaces of the slideable box 1, the holding jacket 16 or the essence box 30 (35, 38).

Figure 7A:
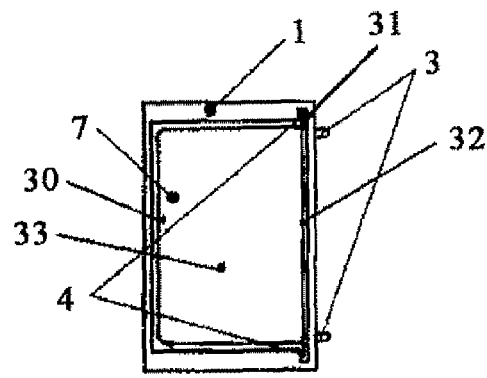
FIG. 7 (FIGS. 7a, 7b and 7c) are schematic views of the structure of the air freshener of the invention.
Figure 7B:
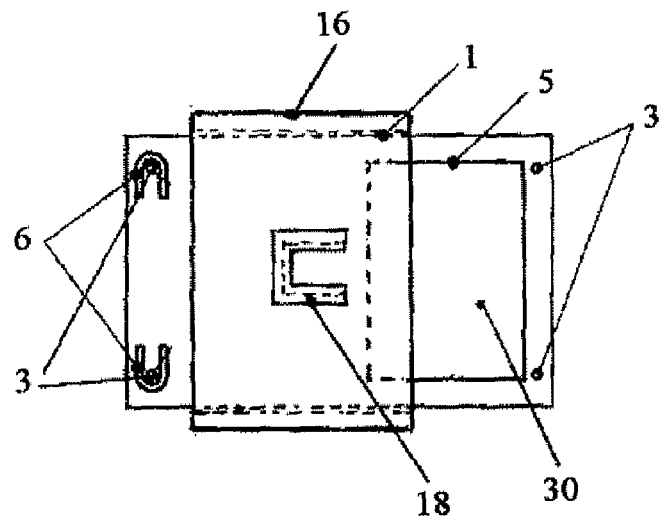
Figure 7C:
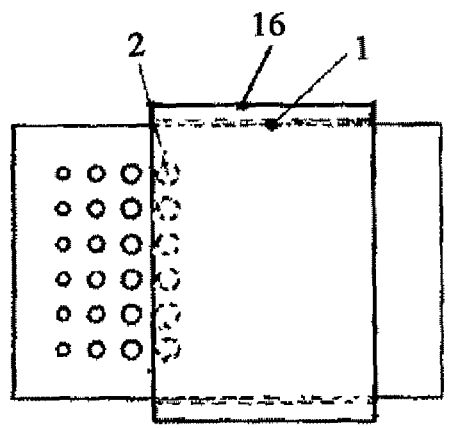

FIGS. 7a, 7b and 7c are schematic views of the structure of the air freshener of the invention FIG. 7a shows that the essence box 30 (35, 38) filled with the liquid essence 33 and sealed with the semi-permeable film 32 is inserted into the space 7 of the slideable box 1 from the opened end of the slideable box 1. At this time, the edge 31 of the essence box 30 (35, 38) is just engaged in the groove 4 of the slideable box 1, so that the whole essence box 30 (35, 38) is inserted closely into the space 7 of the slideable box 1.

FIG. 7b shows that the holding jacket 16 surrounds the slideable box 1. When inserting the slideable box 1, the two projections 3 which are positioned close to the left end (on the back side) of the slideable box 1 are pressed down so that the slideable box 1 can be inserted into the holding jacket 16. When the slideable box 1 is inserted into the holding jacket 16 completely, the two projections returns to their original position by resilience, and the slideable box is confined to slide back and forth between the projections 3 positioned close to both ends of the slideable box 1, so that the slideable box can't drop off. The clip head 24 of the fixing clip 22 or the suction cup 23 is then engaged into the clipping groove 18 of the holding jacket 16. The pair of clip arms 25 of the fixing clip 22 may be clipped on a grille of an air outlet of an air conditioner of a vehicle so that the air freshener of the invention is fixed in place and emits essence gas. The emitted essence gas can be diffused with the help of wind blown from the air outlet of the air conditioner. The suction cup 23 may be fixed on a smooth surface such as a surface of window glass inside a vehicle, or any smooth surface inside a room or vehicle. The figure shows the circumstance in which the holding jacket 16 partially covers the window 5 which allows the essence gas to be released. The window 5 is opened to a maximum and the release rate of essence gas is at its maximum when the holding jacket 16 is pushed and slid to the leftmost side and abuts against the left two projections 3. On the contrary, the window 5 is covered completely and the release rate of the essence gas is at its minimum when the holding jacket 16 is pushed and slid to the rightmost side and abuts against the right two projections 3.

FIG. 7c is a schematic view of the assembled air freshener of the invention.

It can be seen from the above description that the air freshener of the invention is characterized in that the essence box 30 (35, 38) is placed into the slideable box 1 which is fitted closely with the essence box, and then the slideable box 1 is inserted into the holding jacket 16 which is closely fitted with the slideable box. A semi-permeable film 32 for allowing the essence gas to be released is attached on the essence box 30. The area of the portion of the semi-permeable film 32 exposed from the holding jacket 16 can be adjusted by sliding the slideable box 1 back and forth in the holding jacket 16, thereby to adjust the release rate of the essence gas.

The air freshener of the invention can be embodied in many alternative manners. The object of the invention can be achieved as long as the shape of the box body 29 of the essence box 30 (35, 38) matches the shape of the slideable box 1 so that the essence box 30 (35, 38) can be embedded in the slideable box 1 (shown in FIG. 7a), and the holding jacket 16 is shaped to surround the slideable box 1 in a closely fitting manner (shown in FIG. 7a). For this reason, with regard to the essence box 30 (35, 38), the edge 31 of the open side thereof must be in the same plane so that the semi-permeable film 32 can be hermetically attached to the essence box 30 (35, 38). The shapes of other parts of the essence box 30 (35, 38) may be changed, as long as the slideable box 1 having the essence box therein can slide in the holding jacket 16 which is closely fitted with the slideable box 1. In addition, trademarks or aesthetic patterns may be formed or printed on external surfaces of the slideable box 1, the holding jacket 16 or the essence box 30 (35, 38).

What is claimed is:

1. An air freshener, comprising:
    an essence box made of plastics and filled with liquid essence;
    a slideable box molded from thermoplastics;
    a holding jacket molded from thermoplastics; and
    a fixing device;
    wherein the essence box comprises a box body which is suction molded from plastic sheet materials and is shaped and sized to be just embeddable in the slideable box and has an edge in a same plane along a periphery of an opened side of the box body,
    a semi-permeable film, which is impermeable to the liquid essence and permeable to essence gas, is sealed on the plane of the edge along the periphery of the opened side of the box body, and
    an aluminum foil-plastic composite film, which prevents the essence gas from being diffused from the essence box before use, is attached to the semi-permeable film;
    wherein the slideable box is in a shape of a hexahedron having approximately a rectangle cross-section and fitting to the shape of the essence box,
    one side of the slideable box is opened and is sized to just allow the essence box to pass through and has grooves for inserting the edge of the essence box and engaging the essence box,
    a plurality of projections are formed on a back side of the slideable box for defining a sliding range of the slideable box in the holding jacket,
    around the projections positioned close to one end of the slideable box, U-shaped slots are formed for pressing down the projections for inserting the slideable box into the holding jacket and returning to their original position when the slideable box is completely inserted in the holding jacket, and
    a window which allows essence gas to be released is formed on the back side of the slideable box; and
    wherein the holding jacket is in a shape of a hollowed hexahedron having approximately a rectangle cross-section and fitting to the shape of the slideable box,
    a pair of opposite sides are opened and thus the hexahedron forms a jacket,
    the holding jacket just surrounds the slideable box when assembled, and
    a clipping groove for clipping the fixing device is provided on a back side of the holding jacket.

2. The air freshener of claim 1, wherein
the fixing device is a fixing clip having a pair of clip arms and a clip head which can be engaged in the clipping groove of the holding jacket, using said fixing clip the air freshener can be clipped on a grille of an air outlet of an air conditioner in a vehicle.

3. The air freshener of claim 1, wherein
the fixing device is a suction cup having a vacuum suction cup and a clip head which can be engaged in the clipping groove of the holding jacket, using said suction cup the air freshener can be fixed on a window glass or any other smooth surface.

4. The air freshener of claim 3, wherein
the suction cup is made from soft polyvinyl chloride.

5. The air freshener of claim 1, wherein
the box body of the essence box is made of a transparent polyester sheet material, and the slideable box, the holding jacket and the fixing clip are made from polypropylene.

* * * * *